US011116417B2

(12) United States Patent
Takala et al.

(10) Patent No.: US 11,116,417 B2
(45) Date of Patent: Sep. 14, 2021

(54) METHOD AND APPARATUS FOR DETECTION OF INTERFERENCE IN IMPEDANCE BASED MEASUREMENTS

(71) Applicant: GENERAL ELECTRIC COMPANY, Schenectady, NY (US)

(72) Inventors: Panu Antero Takala, Helsinki (FI); Kimmo Henrik Uutela, Helsinki (FI); Mikael Bröckl, Helsinki (FI); Matti Huiku, Helsinki (FI)

(73) Assignee: General Electric Company, Schenectady, NY (US)

( * ) Notice: Subject to any disclaimer, the term of this patent is extended or adjusted under 35 U.S.C. 154(b) by 363 days.

(21) Appl. No.: 16/084,647

(22) PCT Filed: Mar. 15, 2017

(86) PCT No.: PCT/US2017/022464
§ 371 (c)(1),
(2) Date: Sep. 13, 2018

(87) PCT Pub. No.: WO2017/160949
PCT Pub. Date: Sep. 21, 2017

(65) Prior Publication Data
US 2019/0076048 A1 Mar. 14, 2019

(30) Foreign Application Priority Data
Mar. 16, 2016 (GB) ...................................... 1604429

(51) Int. Cl.
*A61B 5/053* (2021.01)
*A61B 5/00* (2006.01)

(52) U.S. Cl.
CPC ............ *A61B 5/053* (2013.01); *A61B 5/7217* (2013.01); *A61B 5/742* (2013.01); *A61B 5/7405* (2013.01)

(58) Field of Classification Search
CPC ..... A61B 5/053; A61B 5/7217; A61B 5/7405; A61B 5/742
(Continued)

(56) References Cited

U.S. PATENT DOCUMENTS 5,474,574 A * 12/1995 Payne .................. A61N 1/3931 607/7
6,442,422 B1 8/2002 Duckert
(Continued)

FOREIGN PATENT DOCUMENTS

GB 1595923 A 8/1981
WO 20100051403 A1 5/2010

OTHER PUBLICATIONS

International Search Report and Written Opinion for PCT/US2017/022464, dated Jun. 8, 2017, 12 pages.
(Continued)

*Primary Examiner* — Daniel L Cerioni
*Assistant Examiner* — Raymond P Dulman

(57) ABSTRACT

A method for detection of interference in impedance based monitoring of a subject by using a monitor is disclosed. The method comprising, connecting the subject to the monitor using one or more leads; and before current is applied to the subject, measuring voltage on the subject via at least one of the one or more leads and if any voltage is detected then the monitor indicates a warning. An impedance based monitor is disclosed, the monitor being connectable to a subject. The monitor is configured to measure voltage on the subject, before any current is applied to the subject, and if any voltage is detected then the monitor is configured to indicate a warning.

12 Claims, 1 Drawing Sheet

10
20
30
40

(58) Field of Classification Search
USPC ......................... 600/509–523, 544–548, 554
See application file for complete search history.

(56) References Cited

U.S. PATENT DOCUMENTS

| | | | | |
|---|---|---|---|---|
| 7,155,196 | B1 | 12/2006 | Beard | |
| 2012/0109001 | A1 | 5/2012 | Ellingson | |
| 2012/0271373 | A1* | 10/2012 | Olson | A61N 1/37 607/28 |
| 2016/0183813 | A1* | 6/2016 | Naima | A61B 5/02416 600/479 |

OTHER PUBLICATIONS

Combined Search and Exam Report for corresponding GB Appln. No. 1064429.9, dated Jun. 30, 2016, 5 pages.

* cited by examiner

METHOD AND APPARATUS FOR DETECTION OF INTERFERENCE IN IMPEDANCE BASED MEASUREMENTS

CROSS-REFERENCE TO RELATED APPLICATIONS

This application is a filing under 35 U.S.C. 371 of international application number PCT/US2017/022464, filed Mar. 15, 2017, which claims priority to GB patent application number 1604429.9, filed on Mar. 16, 2016, the entirety of both disclosures are hereby incorporated by reference.

BACKGROUND

The present disclosure relates to respiration monitoring. More particularly, the present disclosure relates to a method and an apparatus for detection of interference in impedance based measurements. More particularly, the present disclosure relates to a method for detection of interference in impedance based monitoring of a subject, and an impedance based monitor.

Electrical impedance is the measure of the opposition that a circuit presents to a current when a voltage is applied. In quantitative terms, it is the complex ratio of the voltage to the current in an alternating current (AC) circuit. Impedance extends the concept of resistance to AC circuits, and possesses both magnitude and phase, unlike resistance, which has only magnitude. When a circuit is driven with direct current (DC), there is no distinction between impedance and resistance; the latter can be thought of as impedance with zero phase angle.

Monitors used in operating suits and intensive care units use impedance measuring to document a patients ventilator frequency. When connected to such a monitor, a pacemaker sensor may measure the summated impedance signals resulting from the monitor and its own electrical current, falsely interprets the information as an increase in transthoracic impedance, and increases the heart rate accordingly.

Present monitors can interfere with a pacemaker and vice versa. Medical staff using the present monitors does not know if they interfere with a possible pacemaker of a subject. A present monitor addressing this is not known.

SUMMARY

The present disclosure is directed to an impedance based monitor and, a method for detection of interference in impedance based monitoring of a subject by using a monitor. This can be achieved by the features as defined by the independent claims. Further enhancements are characterized in the dependent claims.

According to one embodiment, the present disclosure is directed to a method for detection of interference in impedance based monitoring of a subject by using a monitor. The method comprising, connecting the subject to the monitor using one or more leads; and before any current is applied to the subject by the monitor, measuring voltage on the subject via at least one of the one or more leads and if any voltage is detected then the monitor indicates a warning.

According to one embodiment, the present disclosure is directed to an impedance based monitor, the monitor being connectable to a subject. The monitor is configured to measure voltage on the subject, before any current is applied to the subject by the monitor, and if any voltage is detected then the monitor is configured to indicate a warning.

According to one embodiment, the measuring of voltage is made in a frequency band of operation of the monitor, and in a range of frequency bands different from the frequency band of operation of the monitor. According to one embodiment, if any voltage within a certain frequency band is detected, then the monitor measures voltage on the subject in a different frequency band; and if a free frequency band is detected, then operate the monitor with a current in the free frequency band. According to one embodiment, measuring voltage on the subject in a different frequency band is repeated until a free frequency band for the current is found.

According to one embodiment, wherein when a warning is given, then the monitor requires a manual override to start impedance based monitoring. According to one embodiment, measuring voltage is made in at least a frequency band of operation of one or more of the following devices: the monitor itself, a pacemaker, echocardiography equipment, an apnoea monitor, and an external defibrillator. According to one embodiment, the warning is one or more of a visual indication and an audial indication produced by the monitor.

At least one embodiment disclosed herein provides a method that avoids interference between a pacemaker and a monitor. At least one embodiment disclosed herein provides a monitor that avoids interference between a pacemaker and the monitor. At least one embodiment disclosed herein provides a method how medical staff using a monitor can ensure that they do not interfere with a possible pacemaker, or other device, of a subject, and a monitor for this. At least one embodiment disclosed herein provides a solution that is inexpensive and easy to realize in reality. At least one of the embodiments disclosed herein provides one or more solutions to the problems and disadvantages with the background art. At least one embodiment avoids compromising accuracy of impedance respiration measurement caused by interfering external signal sources. At least one embodiment provides improved patient safety and/or improved quality of respiration monitoring.

Other technical advantages of the present disclosure will be readily apparent to one skilled in the art from the following description and claims. Various embodiments of the present application obtain only a subset of the advantages set forth. No one advantage is critical to the embodiments. Any disclosed or claimed embodiment may be technically combined with any other disclosed or claimed embodiment or embodiments.

BRIEF DESCRIPTION OF THE DRAWINGS

The accompanying drawings illustrate presently exemplary embodiments of the disclosure and serve to explain, by way of example, the principles of the disclosure.

DETAILED DESCRIPTION

Figure 1:
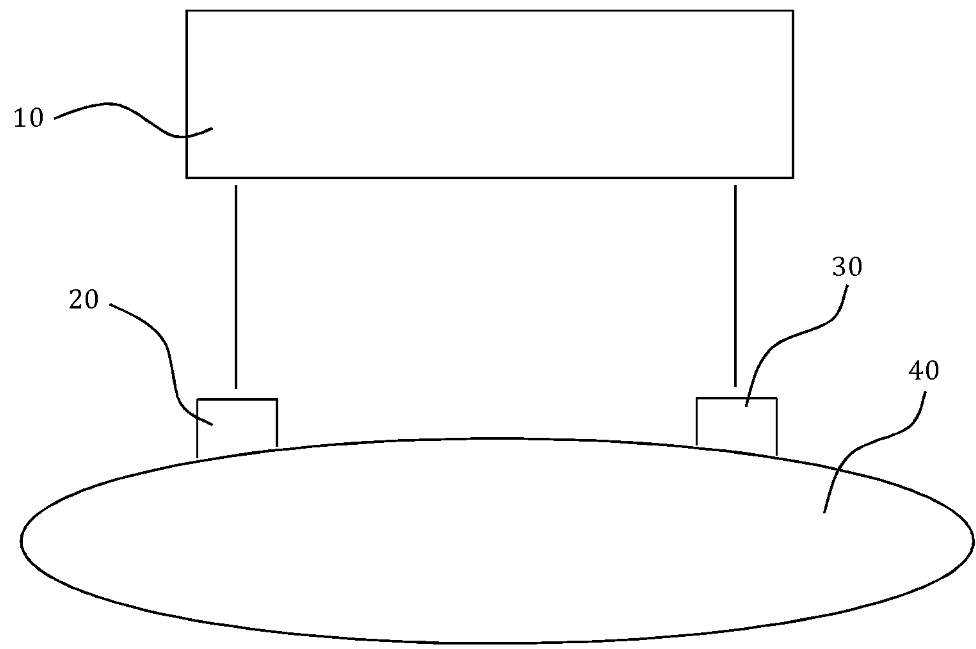
FIG. 1 is a diagrammatic illustration of a monitor according to an exemplary embodiment of the disclosure.

Turning to FIG. 1, according to an embodiment, an impedance respiration monitor 10 measures voltage between electrodes that are attached to a subject 40. The electrodes may for example be leads and/or sensors. The monitor supplies current and measures voltage between the electrodes, for example between a drive electrode 20 and a receive electrode 30, to monitor air flow in lungs. As the subject 40 inhales, air, which is an insulator, enters the lungs and causes the net impedance in the circuit to increase. When the subject exhales, air leaves the lungs and causes the impedance in the circuit to decrease. Thus, a high-frequency AC current is injected into the tissue through the drive electrode 20. The AC current causes a potential difference to develop across the drive electrode 20 and the receive electrode (voltage sensing electrode) 30.

For example, for monitoring a subject's respiration, impedance based respiration monitoring, a monitor may apply a high frequency current to the subject, for example of 100 μA at 10 kHz. A current may be applied in different frequency bands. If another device, for example, a minute volume based cardiac pacemaker, operate in the same frequency range, or within the same frequency band, the two measurements can interfere with each other and cause adverse effects for the subject and/or for respiration monitoring. At least one embodiment relates to detecting the potential interference before the carrier wave of impedance respiration measurement is turned on.

Contrary to this disclosure, a carrier signal is applied to a subject using a normal impedance based respiration monitor when the impedance respiration measurement is turned on. No scan or measurement is done before starting monitoring respiration. If there exists simultaneously a second device that also applies current to the subject, then the two devices can interfere with each other. Contrary hereto, embodiments of the present disclosure avoids this by, before the monitor turns on the carrier wave, the monitor measuring voltage to detect any external carrier wave. In other words, the monitor first listens to the frequency band it is operating in to see if a different device is already using that band. In a case with no external devices, for example when the subject does not have a pacemaker, a zero signal is observed and the carrier wave can be turned on from the monitor without risk of interference. If a signal is detected, for example when the subject has a pacemaker, then a warning message is given to the user of the monitor.

According to one embodiment, the monitor may scan, measure voltage, in more then only the frequency band it is operating in. The monitor may for example scan a range of frequency bands to determine if another device is using any current in a frequency band. If another device operates in a neighbouring frequency band, then this can be detected and the monitor can signal the user of the monitor with a warning. In this way it can be avoided that the monitor interferes with another device, and that another device interferes with the monitor, regardless of the frequency band of the monitor or that another device. Interference with neighbouring frequency bands is avoided.

At least one embodiment avoids adverse events caused to a subject with a pacemaker caused by impedance respiration disturbing the pacing. At least one embodiment avoids compromised accuracy of impedance respiration measurement caused by interfering external signal sources. At least one embodiment improves patient safety. At least one embodiment improves quality of respiration monitoring.

Figure 2:
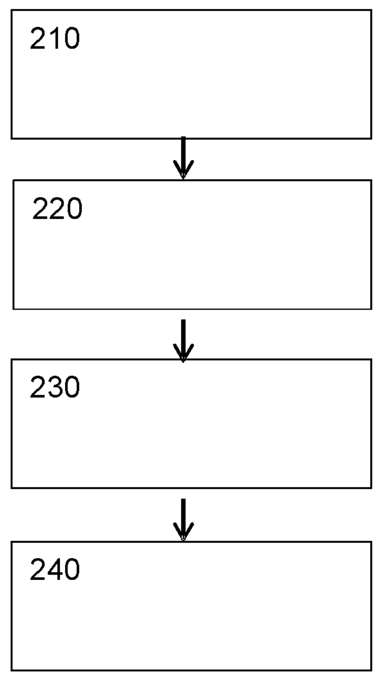
FIG. 2 shows a flow chart of a method according to an exemplary embodiment of the disclosure.

According to one embodiment, a method for detection of interference in impedance based monitoring of a subject by using a monitor is disclosed. This method is illustrated by FIG. 2, box 210. Before any current is applied by the monitor to the subject, the following is done by the monitor. The monitor measures, scans for, voltage on the subject. When the receive electrode 30, sensor 30, is attached to the subject, then the monitor measures voltage, and it does so before any current is applied by the monitor via any lead. The measuring of voltage on the subject is made in at least one frequency band of operation of the monitor. The monitor scans in this way to detect an external carrier wave, a high frequency AC signal other than the carrier wave used by the monitor itself when monitoring respiration. If such voltage is detected then the monitor indicates a warning. Hereby a user can take appropriate actions, such as checking for a pacemaker in the subject. The monitor measures if there is any voltage in any of the leads of the monitoring system before any carrier wave is applied. Thus, the first operation that the monitor does before allowing any current to be applied, is the scanning of any current already present by measuring voltage. If any current is detected, then the monitor blocks to use the monitor and gives a warning to the user of the monitor. If no current is detected, then the monitor allows monitoring. In practice, as with measurements, some voltage may be detected due to, for example measurement noise, muscle noise, cardiac activity, or similar. Such noise is naturally not part of the voltage detected for indicating a warning as described. Such noise may be excluded by filtering, and/or disregarded because it is not above a pre-determined amplitude and/or frequency threshold. In other words, to indicate a warning if any voltage is detected excludes noise in the detected voltage, such as measurement noise, muscle noise, cardiac activity, or similar.

According to one embodiment, the measuring of voltage is also made in a range of frequency bands of operation different from the frequency band of operation of the monitor. This embodiment is also represented by box 210 in FIG. 2. This is in addition to the frequency band of operation of the monitor. In this way the monitor scans for a current or voltage in a range of frequency bands to determine if another device is using any other frequency band. The monitor may in this way detect if another device interferes with a neighbouring frequency band. The range of frequency bands of operation different from the frequency band of operation of the monitor may be the range of operation of other devices using electric impedance measuring, such as for example, echocardiography equipment, apnoea monitors, and external defibrillators. If an external carrier wave at a given frequency band is detected, embodiments herein could comprise the step of not using such a detected frequency band, and instead use a different frequency band that has been detected to be available by the monitor. The monitor may switch the operating frequency band to a frequency band that the monitor has detected is free.

According to one embodiment, the method may further comprise the following. If any voltage is detected, then the monitor measures voltage on the subject in a different frequency band. That is, in a frequency band different from the previous frequency band, or bands if several measurements have been done. If no voltage is measured, then the monitor can be operated within such a free frequency band. This embodiment is represented by box 220 in FIG. 2. In other words, if a current is detected, then the monitor can try one or more different frequency ranges until it finds a free frequency range that it can use. The user may be informed hereof by an indication, such as a warning indication and/or what frequency range to use for monitoring respiration.

According to one embodiment, especially according to the previous embodiment, the method may further comprise the following. The step of measuring voltage on the subject in a different frequency band, then the previous frequency bands, is repeated until a frequency band is found where no voltage is measured. With a different frequency band is meant a free frequency band that is different from the previous frequency band used. This embodiment is represented by box 230 in FIG. 2. In this way, if an external carrier wave at a given frequency band is found and a warning is indicated not to start measurement with that frequency, then the monitor could switch to a different band and measure if it is safe to start monitoring with that new frequency. Hereby interference is avoided.

According to one embodiment, the monitor requires a manual override to continue impedance monitoring. This embodiment is represented by box 240 in FIG. 2. When a warning is indicated, then, for safety reasons, a manual override, a physical action by the user of the monitor, must be made to measure impedance on that frequency range where an external carrier wave was detected.

According to one embodiment, the at least one frequency band of operation is a frequency band of operation of one or more of the following devices: the monitor itself, pacemaker, echocardiography equipment, apnoea monitor, and external defibrillator. The monitor measures voltage, scans for current at certain frequency ranges, corresponding to frequency bands used by one or more of such devices. The method may include that the monitor is configured to detect voltage characteristic of these devices. Hereby the method ensures that measurements are made to detect known devices.

According to one embodiment, the warning is one or more of a visual indication and an audial indication produced by the monitor. The warning may be a sounding alarm. In addition hereto, or separately, the warning may be a visual indication, such as a light or an indication on a screen of the monitor. The warning may additionally be that the monitor does not allow monitoring to start.

According to one embodiment, an impedance based monitor is provided. The monitor may be for a patient, to monitor respiration. The monitor is connectable to a subject, a patient. Such a connection can be made by a wireless or cable lead (sensor, electrode). The monitor may be configured to detect other devices using impedance based monitoring relating to the subject in question. The monitor may be configured to measure voltage, scanning for current, on the subject in at least one frequency band of operation of the monitor, before any current is applied to the subject. This is to detect an external carrier wave. That is a carrier wave other than the carrier wave produced by the monitor itself. If such voltage is detected then the monitor is configured to indicate a warning. This configuration may be made by programming the monitor and/or configuring the monitor's circuit board.

According to one embodiment, the monitor is further configured to measure voltage in a range of frequency bands of operation different from the frequency band of operation of the monitor. The monitor does not only measure voltage in the frequency bands of the monitor, but in addition to the frequency band of operation of the monitor, the monitor is also configured to measure voltage in a range of frequency bands of operation different from the frequency band of operation of the monitor. This is to detect other devices that produce a current within the subject, and where that current could interfere with the monitor or the monitor could interfere with such other device.

According to one embodiment, the monitor is further configured to, if any voltage within a certain frequency band is detected, measuring voltage on the subject in a different frequency band. If no voltage is measured, if a free frequency band is detected, then the monitor is configured to operate with a current in such a free frequency band. The monitor may be configured to repeat measuring voltage on the subject in a different frequency band, until a frequency band is found where no voltage is measured. Such a monitor would provide a possibility that when an external carrier wave at a given frequency band is found, the monitor will not use or start the measurement with that frequency, but instead the monitor would switch to a different frequency band and detect if it is safe to start monitoring with that new frequency.

According to one embodiment, the monitor may be configured to require a manual override to start impedance monitoring. When a warning is given, e.g. when an external current at a given frequency band is found, then the monitor may require that a user must make a physical interaction with the monitor, e.g. press a button, to confirm that the monitor should use, continue to use, that frequency band for a carrier wave for monitoring respiration.

According to one embodiment, the monitor is configured to measure voltage in at least one frequency band of operation of one or more of the following devices: the monitor itself, pacemaker, echocardiography equipment, apnoea monitor, and external defibrillator. The configuration of the monitor may include that the monitor is configured to detect voltage characteristic of these devices. Hereby the impedance based monitor is configured to detect interference with these devices that could cause interference.

According to one embodiment, the monitor is further configured to produce the warning as one or more of a visual indication and an audial indication. This could for example be a sounding alarm alone or in combination with a light. Another example would be a flashing light with or without a sounding alarm.

According to one embodiment, the monitor and the method measures voltage, before any current is applied, in at least one frequency band of operation of the monitor to detect an external carrier wave, an existing current, and if such current is detected then the monitor indicates a warning. When the respiration monitor is attached to the subject via two or more leads, electrodes/sensors, then the monitor scans for any current, carrier waves, in the frequency bands of operation of the monitor to detect any external devices before the respiration monitoring starts.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method for detection of interference in impedance based monitoring of a subject by using a monitor, comprising:

connecting the subject to the monitor using one or more leads; and before any current is applied to the subject by the monitor, measuring a voltage on the subject via at least one of the one or more leads and if any voltage is detected then the monitor indicates a warning, wherein measuring the voltage on the subject is repeated in different frequency bands until a free frequency band is found.

2. The method of claim 1, wherein the measuring of the voltage is made in a frequency band of operation of the monitor, and in a range of frequency bands different from the frequency band of operation of the monitor.

3. The method of claim 1, further comprising, if the free frequency band is detected, operating the monitor with a current in the free frequency band.

4. The method of claim 1, wherein when a warning is given, then the monitor requires a manual override to start impedance based monitoring.

5. The method of claim 1, wherein measuring the voltage is made in at least a frequency band of operation of one or more of the following devices: the monitor itself, a pacemaker, echocardiography equipment, an apnoea monitor, and an external defibrillator.

6. The method of claim 1, wherein the warning is one or more of a visual indication and an audial indication produced by the monitor.

7. An impedance based monitor, the impedance based monitor configured to measure a voltage on a subject, before any current is applied to the subject by the impedance based monitor, and if any voltage is detected then the impedance based monitor is to indicate a warning, wherein measuring the voltage on the subject is repeated in different frequency bands until a free frequency band is found.

8. The impedance based monitor of claim 7, wherein the impedance based monitor is to measure the voltage in a frequency band of operation of the impedance based monitor, and in a range of frequency bands different from the frequency band of operation of the impedance based monitor.

9. The impedance based monitor of claim 7, wherein the impedance based monitor is to, if a free frequency band is detected, operate the impedance based monitor with a current in the free frequency band.

10. The impedance based monitor of claim 7, wherein when a warning is given, then the impedance based monitor is to require a manual override to start impedance monitoring.

11. The impedance based monitor of claim 7, wherein the impedance based monitor is to measure a voltage in at least a frequency band of operation of one or more of the following devices: the impedance based monitor itself, a pacemaker, echocardiography equipment, an apnoea monitor, and an external defibrillator.

12. The impedance based monitor of claim 7, wherein the impedance based monitor is to produce the warning as one or more of a visual indication and an audial indication.

* * * * *